(12) United States Patent
Utsch et al.

(10) Patent No.: US 9,003,590 B2
(45) Date of Patent: Apr. 14, 2015

(54) HANDLE SECTION OF A SMALL ELECTRIC DEVICE AND SMALL ELECTRIC DEVICE

(75) Inventors: Joern Utsch, Eschborn (DE); Uwe Schober, Schlossborn (DE); Frank Ziegler, Karben (DE); Norbert Schaefer, Frankfurt am Main (DE)

(73) Assignee: Braun GmbH, Kronberg (DE)

( * ) Notice: Subject to any disclaimer, the term of this patent is extended or adjusted under 35 U.S.C. 154(b) by 201 days.

(21) Appl. No.: 13/190,284

(22) Filed: Jul. 25, 2011

(65) Prior Publication Data

US 2012/0042742 A1    Feb. 23, 2012

(30) Foreign Application Priority Data

Jul. 23, 2010    (EP) .................................. 10007716

(51) Int. Cl.
*A47L 21/02*    (2006.01)
*A61C 17/22*    (2006.01)
*A61C 17/34*    (2006.01)
*H02K 33/10*    (2006.01)

(52) U.S. Cl.
CPC ........... *A61C 17/222* (2013.01); *A61C 17/3436* (2013.01); *H02K 33/10* (2013.01)

(58) Field of Classification Search
USPC ................ 74/25; 15/22.1, 22.2, 28, 29, 167.1
See application file for complete search history.

(56) References Cited

U.S. PATENT DOCUMENTS

| | | |
|---|---|---|
| 5,404,608 A | 4/1995 | Hommann |
| 5,448,792 A | 9/1995 | Wiedemann et al. |
| 5,504,959 A | 4/1996 | Yukawa et al. |
| 5,524,312 A | 6/1996 | Tan et al. |
| 5,732,432 A | 3/1998 | Hui |
| 5,836,030 A | 11/1998 | Hazeu et al. |
| 5,934,908 A | 8/1999 | Woog et al. |
| 6,098,288 A | 8/2000 | Miyagawa et al. |
| 6,446,294 B1 | 9/2002 | Specht |
| 6,813,793 B2 | 11/2004 | Eliav |
| 6,845,537 B2 * | 1/2005 | Wong .............................. 15/22.1 |
| 6,889,401 B2 | 5/2005 | Fattori et al. |
| 6,966,093 B2 | 11/2005 | Eliav et al. |

(Continued)

FOREIGN PATENT DOCUMENTS

DE    1196 03 851 A1    8/1997
DE    197 27 018 B4    4/2007

(Continued)

OTHER PUBLICATIONS

PCT International Search Report dated Oct. 28, 2011.

*Primary Examiner* — William Kelleher
*Assistant Examiner* — Emily Cheng
(74) *Attorney, Agent, or Firm* — George Henry Leal; Vladimir Vitenberg

(57) ABSTRACT

A handle section of a small electric device is described that has a handle housing in which a drive unit is disposed, a first connector element extending from the housing being adapted for connection with an attachment section, the first connector element being coupled to the drive unit; a second connector element extending from the housing being adapted for connection with the attachment section, the second connector element being coupled to the drive unit, wherein the first connector element linearly reciprocates relative to the housing during operation and the second connector element linearly reciprocates relative to the housing with a 180 degrees phase shift with respect to the first connector element.

8 Claims, 7 Drawing Sheets

(56) References Cited

U.S. PATENT DOCUMENTS

| | | |
|---|---|---|
| 6,973,694 B2 | 12/2005 | Schutz et al. |
| 7,117,555 B2 | 10/2006 | Fattori et al. |
| 7,140,058 B2 | 11/2006 | Gatzemeyer et al. |
| 7,258,747 B2 | 8/2007 | Vago et al. |
| 7,288,863 B2 | 10/2007 | Kraus |
| 7,315,098 B2 | 1/2008 | Kunita et al. |
| 7,430,776 B2 | 10/2008 | Eliav |
| 7,443,059 B2 | 10/2008 | Kobayashi et al. |
| 7,448,108 B2 | 11/2008 | Gatzemeyer et al. |
| 7,474,018 B2 | 1/2009 | Shimizu et al. |
| 7,520,016 B2 | 4/2009 | Kressner |
| 7,552,497 B2 | 6/2009 | Gatzemeyer et al. |
| 7,646,117 B2 | 1/2010 | Shimizu et al. |
| 7,654,271 B2 | 2/2010 | Wyatt et al. |
| 7,687,944 B2 | 3/2010 | Benning et al. |
| 7,698,771 B2 | 4/2010 | Gall |
| 7,784,136 B2 | 8/2010 | Gatzemeyer et al. |
| 7,810,199 B2 | 10/2010 | Kressner |
| 7,827,644 B2 | 11/2010 | Eliav |
| 7,861,348 B2 | 1/2011 | Chan |
| 7,876,003 B2 | 1/2011 | Bax |
| 7,877,832 B2 | 2/2011 | Reinbold |
| 2003/0097723 A1 | 5/2003 | Li |
| 2003/0182743 A1 | 10/2003 | Gatzemeyer et al. |
| 2004/0060135 A1 | 4/2004 | Gatzemeyer et al. |
| 2004/0060137 A1 | 4/2004 | Eliav |
| 2004/0084063 A1 | 5/2004 | Vago et al. |
| 2004/0123409 A1 | 7/2004 | Dickie |
| 2004/0128781 A1 | 7/2004 | Kunita et al. |
| 2004/0255409 A1* | 12/2004 | Hilscher et al. ............... 15/22.1 |
| 2005/0011023 A1 | 1/2005 | Chan |
| 2005/0102776 A1 | 5/2005 | Mathur |
| 2005/0235438 A1 | 10/2005 | Motohashi et al. |
| 2006/0027246 A1 | 2/2006 | Wilkinson |
| 2006/0032006 A1 | 2/2006 | Brown et al. |
| 2006/0048315 A1 | 3/2006 | Chan et al. |
| 2007/0000079 A1* | 1/2007 | Mori et al. ..................... 15/22.2 |
| 2007/0130705 A1 | 6/2007 | Chan et al. |
| 2007/0272269 A1* | 11/2007 | Wyatt et al. ................... 132/320 |
| 2008/0083075 A1 | 4/2008 | Dickie |
| 2008/0254407 A1 | 10/2008 | Benning et al. |
| 2008/0276390 A1 | 11/2008 | Hegemann et al. |
| 2009/0049626 A1 | 2/2009 | Eliav et al. |
| 2009/0056045 A1 | 3/2009 | Cho |
| 2009/0070948 A1 | 3/2009 | Bax |
| 2009/0211043 A1 | 8/2009 | Kressner |
| 2010/0132139 A1 | 6/2010 | Jungnickel |
| 2010/0306934 A1 | 12/2010 | Headstrom |
| 2011/0005014 A1 | 1/2011 | Kressner |
| 2011/0080061 A1 | 4/2011 | Bax |
| 2011/0258793 A1* | 10/2011 | Jousma et al. ................ 15/22.2 |

FOREIGN PATENT DOCUMENTS

| | | | |
|---|---|---|---|
| DE | 102006038608 A1 * | 2/2008 | ............ A61C 17/34 |
| EP | 1 737 110 A1 | 12/2006 | |
| JP | 9-252843 | 9/1997 | |
| JP | 2007-000693 | 1/2007 | |
| JP | 2010-035315 | 2/2010 | |
| NL | C 1030139 | 10/2005 | |
| WO | WO 2008/015616 A2 | 2/2008 | |
| WO | WO 2008/019864 A2 | 2/2008 | |
| WO | WO 2011/044858 A1 | 4/2011 | |

* cited by examiner

HANDLE SECTION OF A SMALL ELECTRIC DEVICE AND SMALL ELECTRIC DEVICE

FIELD OF THE INVENTION

The present invention is concerned with a handle section of a small electric device and a small electric device having such a handle section and an attachment section coupled to the handle section.

BACKGROUND OF THE INVENTION

It is known to provide a handle section of a small electric device such as a tooth cleaning device with two shafts to which a head of the small electric device can be coupled to generate two independent motions of the head. Patent application WO 2008/125269 A2 generally speaks about such a design.

It is a desire of the present disclosure to provide a handle section of a small electric device and a small electric device that are improved over the known devices or that at least provide an alternative to the known devices.

SUMMARY OF THE INVENTION

In some embodiments, a handle section of a small electric device is proposed that has a handle housing in which a drive unit is disposed. A first connector element extends from the housing and is adapted for connection with an attachment section. The first connector element is coupled to the drive unit. A second connector element extends from the housing and is adapted for connection with the attachment section. The second connector element is coupled to the drive unit. The first connector element linearly reciprocates relative to the housing during operation and the second connector element linearly reciprocates relative to the housing with a 180 degrees phase shift with respect to the first connector element.

In some embodiments, a small electric device is proposed that has a handle section as proposed and further an attachment section coupled to the first connector element and the second connector element, wherein the coupling is optionally realized as a detachable coupling.

BRIEF DESCRIPTION OF THE DRAWINGS

The present disclosure is further elucidated by a detailed explanation of general embodiments and example embodiments and by reference to figures showing example embodiments. In the figures

DETAILED DESCRIPTION OF THE INVENTION

Figure 1:
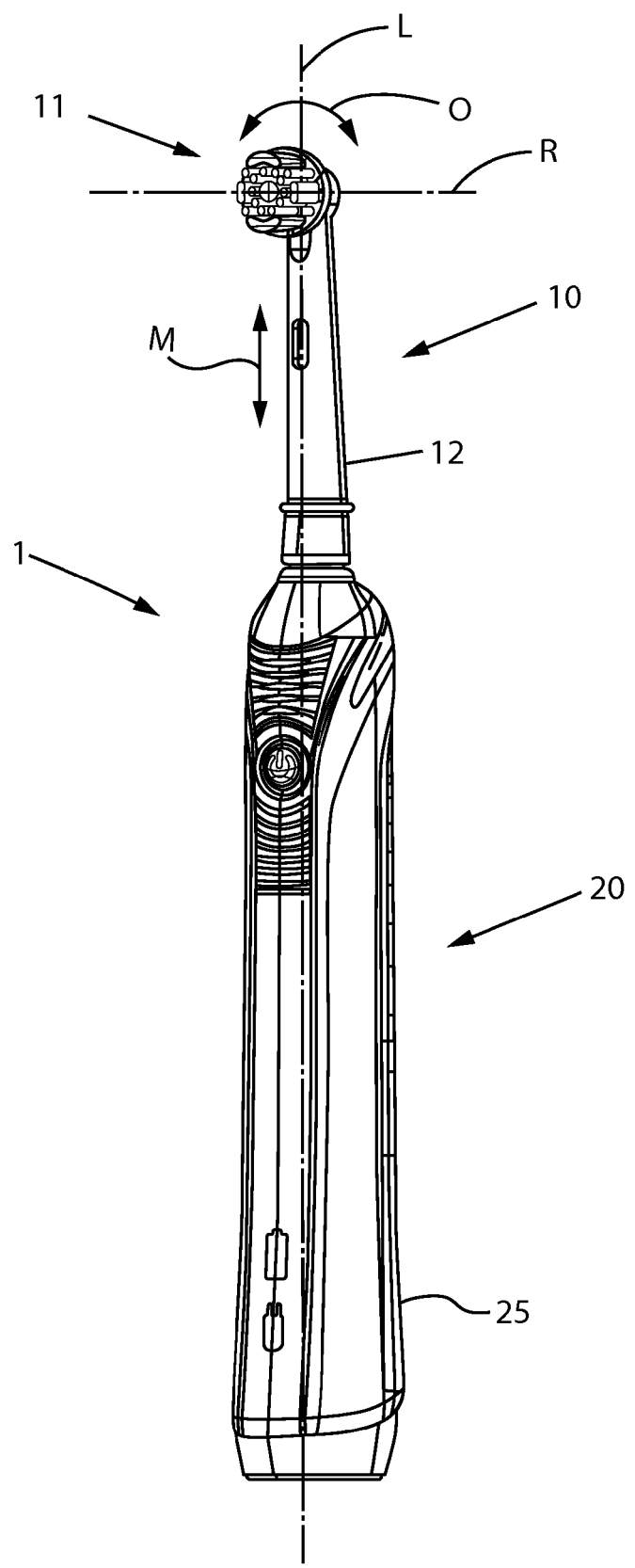
FIG. 1 is a depiction of an example embodiment of a small electric device having a handle section and an attachment section.

The proposed handle section and the proposed small electric device will be described by a more general description of example embodiments and further by more detailed descriptions of example embodiments. It is to be understood that features described with reference to any example embodiment can also be utilized together with features described for another example embodiment as long as this does not contradict the gist and scope of the present disclosure.

A small electric device is in an example embodiment realized as an oral hygiene device such as an electric toothbrush, an electric flosser, an electric tongue scraper, etc.

A handle section in accordance with some embodiments has two connectors that during operation provide linear reciprocating motion with opposite phase. This can be used to impose two different movements onto an attachment section as the first connector may be coupled with a housing of the attachment section and the second connector may be coupled with a functional element of the attachment section. The coupling between the handle section and the attachment section is in one embodiment realized as a detachable coupling. In an example embodiment, the first and the second connector are coaxially arranged. In an example embodiment, a first drive and a second drive form the drive unit. In an example embodiment, the drive unit is a resonant drive and a first moving part of the resonant drive forms a first drive and a second moving part of the resonant drive forms a second drive. As will be explained further below, a resonant drive having two moving parts may be designed such that vibrations generated by the moving parts and transmitted onto a housing of the handle section that is gripped by a user during operation cancel each other at least to a certain amount, optionally wherein the vibrations cancel each other virtually completely. The first moving part and the second moving part may be coupled by a spring arrangement, which spring arrangement may be designed so that the phase between the moving parts is 180 degrees during operation. It is stated by way of example that a feature such as the coaxial arrangement of the first and second connector elements can be well combined with the feature of realizing the drive as a resonant motor having a first and a second moving part. Such combination of features of the more general embodiments and/or the more detailed embodiments discussed further below can be combined with each other.

In an example embodiment, the first connector and/or the second connector moves during operation with a frequency of at least 100 Hz, optionally with at least 110 Hz, further optionally with at least 120 Hz, yet further optionally with at least 130 Hz, yet even further optionally with at least 140 Hz or even further optionally with at least 150 Hz. In an example embodiment, the first connector element moves during operation with a frequency in the range of between about 150 Hz and about 170 Hz. In an example embodiment, the first connector element moves during operation with a frequency of not more than about 250 Hz, optionally with a frequency of not more than about 200 Hz.

In an example embodiment, a small electric device as proposed has an attachment section that is equipped with a functional element that is mounted at a housing of the attachment section for driven movement during operation. In an example embodiment, the housing of the attachment section is coupled to the first connector of the handle section so that the housing will be driven into a linear reciprocation during operation, and the functional element is coupled with the second connector. In an example embodiment, the functional element is mounted for rotation or oscillatory rotation around a rotation axis, optionally wherein the rotation axis is essentially perpendicular to a longitudinal axis along which the housing linearly reciprocates. In an example embodiment, the attachment section comprises a gear unit for transforming the linear reciprocating movement provided by the second connector during operation. Optionally, the gear unit may have a shaft element that is on a first end eccentrically coupled to the functional element with respect to a rotation axis around which the functional element will be moved during operation and which shaft element is coupled to the second connector at a second end, optionally wherein the coupling to the second connector is realized as a detachable coupling.

In an example embodiment, the first and/or second connector provides a linear reciprocating movement with a peak amplitude within a range of between about ±0.1 mm around a centre position (i.e. the maximum displacement of the first connector element is 0.1 mm in the positive movement direction and −0.1 mm in the negative movement direction) to about ±1.0 mm. Optionally, this range may be chosen to lie between about ±0.2 mm and about ±0.5 mm. The peak amplitude, in some embodiments, may be greater than about 0.1 mm, greater than about 0.2 mm, greater than about 0.5 mm, greater than about 0.75 mm, greater than about 1.0 mm or any number or any range within or including these values.

In an example embodiment, the average absolute velocity of the first connector (or the second connector) lies in a range of between about 60 mm/s to about 240 mm/s, optionally in a range of between about 100 mm/s to about 240 mm/s and further optionally in a range of between about 120 mm/s to about 240 mm/s, or any numbers or any ranges within and/or including the values above. As will be explained further below, such velocities may lead to improved performance of the small electric device. In an example embodiment, the attachment section has at least a cleaning element that is realized as a filament that has a resonance frequency in the range of between about 200 Hz and about 800 Hz. The resonance frequency of the cleaning elements is discussed hereafter.

The proposed handle section and the proposed small electric device will now be explained in more detail with reference to figures showing example embodiments.

FIG. 1 is a depiction of an example embodiment of a small electric device 1 as proposed, which small electric device 1 has a handle section 20 and an attachment section 10. The attachment section 10 may be detachably connected to the handle section 20 so as to enable easy replacement of the attachment section 10, e.g. when the attachment section 10 is worn out or when a different attachment section is to be used (e.g. by a different user). The small electric device 1 is here realized as an oral hygiene device in the form of an electric toothbrush.

The attachment section 10 has a functional element 11, here realized as a brush head for cleaning parts of the oral cavity. As shown, the functional element 11 may be mounted at a housing 12 of the attachment section 10 for driven rotation or oscillatory rotation as indicated by double arrow O around a rotation axis R during operation of the small electric device 1. The rotation axis R is in an example embodiment essentially perpendicular to a longitudinal axis L of the small electric device 1. The attachment section 10 is mounted at a handle section 20. In an example embodiment, the attachment section 10 is mounted at the handle section 20 for driven movement, e.g. for a driven linear reciprocation as indicated by double arrow M along an axis that essentially coincides with the longitudinal axis L. Details of the connection between attachment section and handle section are discussed below for an example embodiment.

Figure 2:
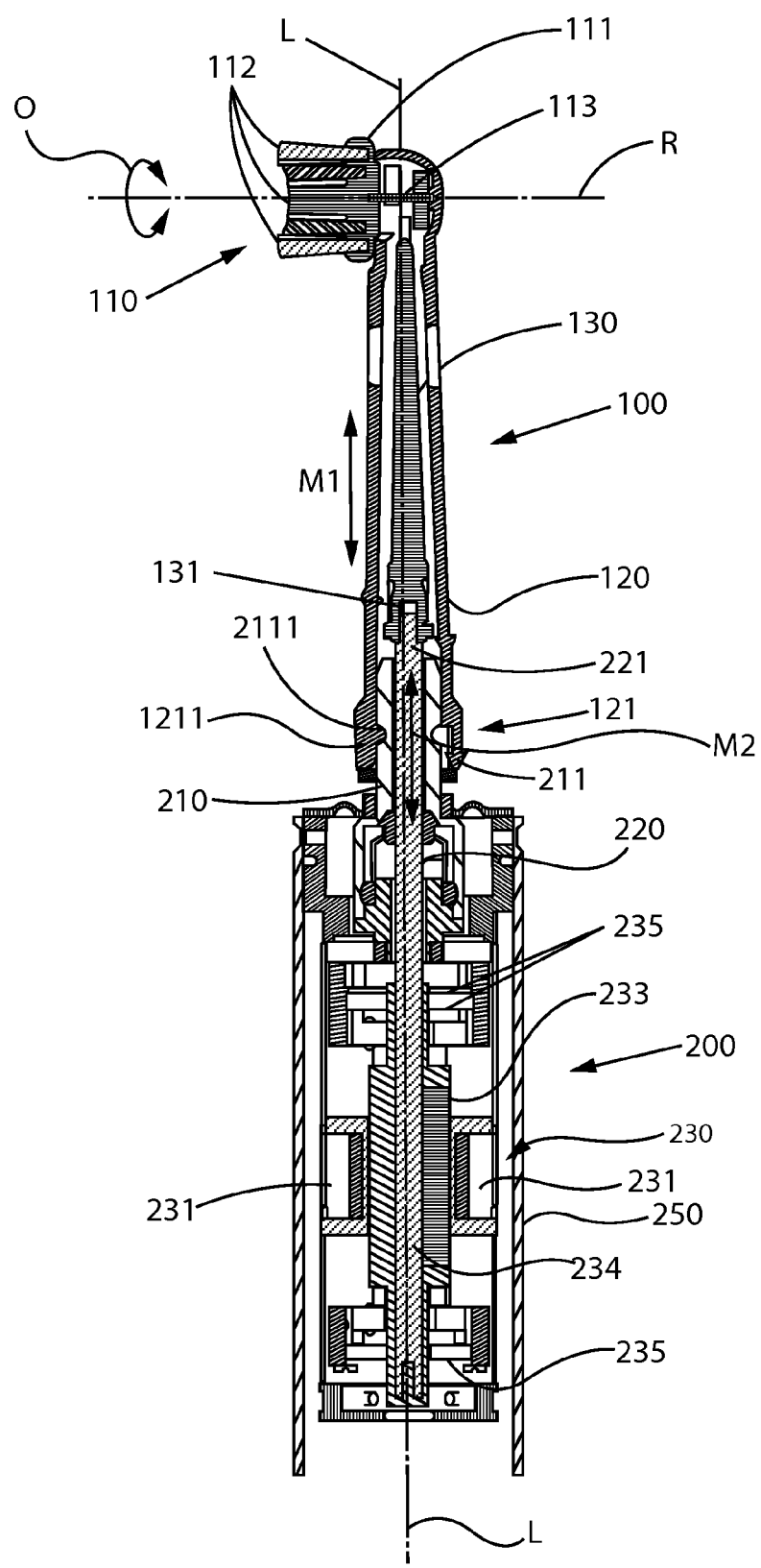
FIG. 2 is a lateral cross sectional cut through an example embodiment of a small electric device realized as an oral hygiene device comprising a handle section and an attachment section.
Figure 3:
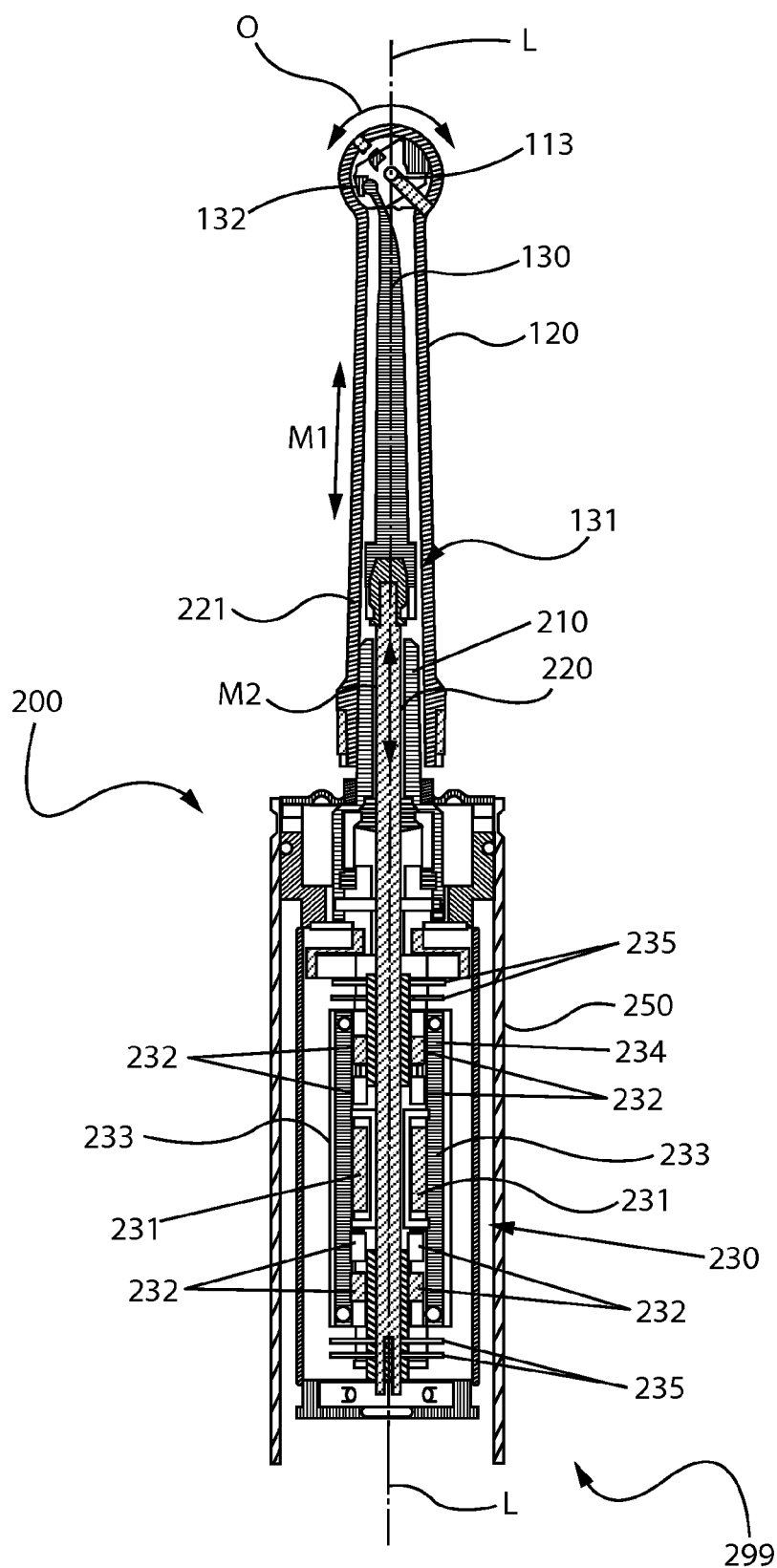
FIG. 3 is a transverse cross sectional cut through the small electric device shown in FIG. 2.

FIG. 2 is a lateral cross sectional cut through an example embodiment of a small electric device as proposed, in this example embodiment realized as an oral hygiene device in the form of an electric toothbrush. FIG. 3 is a transversal longitudinal cross sectional cut through the small electric device shown in FIG. 2. In the following sections it is referred to FIGS. 2 and 3.

An attachment section 100 is detachably attached to a handle section 200. The attachment section 100 has a functional element 110, here realized as a brush head, which functional element 110 is mounted at a housing 120 of the attachment section 100 such that driven rotation or oscillatory rotation—as indicated by double arrow O—of the functional element 110 around a rotation axis R during operation is enabled. In the shown embodiment, the functional element 110 has a carrier element 111 on which at least a cleaning element 112 is mounted. The carrier element 111 is pivot mounted on an axle 113, which axle 113 extends along the rotation axis R. The housing 120 of the attachment section 100 has a connector assembly 121 for detachably attaching the attachment section 100 to the handle section 200. In some embodiments, the connector assembly 121 has a snap hook 1211 for establishing a connection with the handle section 200. Additionally or alternatively, other mounting elements may be present such as at least one of the following group including a bayonet coupling element, a magnetic coupling element, a screw coupling element etc.

A shaft element 130 is arranged within the housing 120. The shaft element 130 is on a first end coupled to the functional element 111 and has a connector assembly 131 on a second end by which the shaft element 130 is detachably attached to the handle section 200. The shaft element 130 may be eccentrically coupled to the functional element 110 with respect to the rotation axis R that is defined by the axle 113. The shaft element 130 may be coupled by a coupling element 132 that can be a coupling pin that extends into a cavity formed in the carrier element 111. The connector assembly 131 may comprise at least one of a snap-fit element, a magnetic coupling element, a screw-coupling element etc. for realizing a snap-fit coupling, a magnetic coupling, a screw coupling etc.

In the shown example embodiment, the handle section 200 has a drive unit 230, a first connector 210 and a second connector 220. As shown, the housing 120 may be detachably connected, as described above, to the first connector 210, and the shaft element 130 may be detachably connected, as described above, to the second connector 220.

Here, the first and the second connectors 210, 220 are coaxially arranged, but generally they can be arranged in any suitable manner, e.g. they can be arranged side-by-side. The first connector 210 may be realized as a plastic shaft element having a through-hole in a longitudinal direction. The first connector 210 has a connector assembly 211 that is here arranged for coupling with the connector assembly 121 provided at the housing 120 of the attachment section 100. The connector assembly 211 may be realized as a groove 2111 into which a snap hook 1211 provided at the housing 120 of the attachment section 100 can snap into. Any suitable kind of coupling partners can be chosen instead of snap hook and groove, e.g. the connector assembly may comprise a bayonet coupling element, a magnetic coupling element, a screw coupling element etc.

The second connector 220 may be realized as a (e.g. metal) shaft element extending through the through-hole provided in the first connector 210. Here, the second connector 220 has a connector assembly 221 that in an example embodiment is detachably coupled with the connector assembly 131 provided at the second end of the shaft element 130 of the attachment section 100. As was discussed with respect to the first connector 210, the connector assembly 221 may comprise a snap-fit coupling element, a magnetic coupling element, a bayonet coupling element, or a screw coupling element, etc., or combinations thereof. The connector assemblies provided at the first and second connectors should fit to the respective connector assemblies provided at the attachment section.

The first and the second connectors 210 and 220 may each be coupled to a drive unit 230 provided in a hollow housing 250 of the handle section 200 as will be explained in more detail in the following. During operation, in some embodiments, the drive unit 230 drives the first connector 210 into a linear reciprocating movement as indicated by double arrow M1 (which movement is transmitted to the housing 120 of the attachment section 100 so that the whole attachment section 100 performs the linear reciprocating movement). Additionally, the drive unit 230 can drive the second connector 220 into a linear reciprocating movement as indicated by double arrow M2 that has a 180 degrees phase shift with respect to the movement of the first connector 210. As the second connector 220 is here coupled to the shaft element 130, the linear reciprocating movement is transmitted to the functional element 110, where this movement is transformed into an oscillatory rotation O of the functional element around the rotation axis R.

The drive unit 230 is in the shown example embodiment realized as a resonant drive. A resonant drive that can be utilized in an example embodiment is described in patent application EP 10007716.3.

The drive unit 230 comprises a first moving part 233 and a second moving part 234 that in this example embodiment also forms the second connector 220. The second moving part 234 here extends along the longitudinal axis L and may be at least partially made of a magnetizable material such as ferritic or martensitic steel or iron. The first moving part 233 is operatively coupled, optionally fixedly connected to the first connector 210 so that a movement of the first moving drive part 233 is transmitted during operation to the first connector 210. Permanent magnets 232 may be fixedly secured to the first moving part 233. The drive unit 230 has a coil 231 that is in the shown example fixedly secured at the housing 250 of the handle section 100 (while in an alternate embodiment, the coil 231 may be secured at the second moving part 234 instead of at the housing 250).

An alternating current can be fed to the coil 231 during operation. For those embodiments where the second moving part 234 comprises magnetizable material, the magnetizable material is at least partially magnetized and a magnetic force builds up between the first moving part 233 (at which the permanent magnets 232 are secured) and the second moving part 234. This force between the first and the second moving parts 233, 234, respectively, induces a motion of both parts with a phase shift of 180 degrees. By alternating the polarity of the current and by having return forces of spring elements (details about the springs are given below) acting on the first and second moving parts 233, 234, an oscillating motion is created.

The spring constants of the springs between the moving parts and the respective masses of the moving parts are relevant factors defining the resonance frequency of the drive unit 230. In some embodiments, the drive unit 230 is driven at or approximately at resonance frequency (i.e. the driving frequency and thus the frequency with which the drive unit 230 moves is at or approximately at the resonance frequency).

In some embodiments, the first and second moving parts 233 and 234 are coupled to the housing 250 and to each other by mounting springs 235. By coupling both the first and second moving parts 233 and 234, respectively, to the housing 250, the vibrations transmitted to the housing 250 during operation can cancel each other to a certain extent, optionally essentially completely. Additionally, the springs 235 can assist in causing the first and second moving drive parts 233 and 234 move with a 180 degrees phase shift relative to each other. In another example embodiment, the coil 231 is fixedly secured to the second moving part 234.

As can be seen in FIG. 3, when the second connector 220 (i.e. in the shown embodiment the second moving part 234) moves upwards (i.e. towards the functional element), then the first connector 210 that moves with a 180 degrees phase shift with respect to the second connector 220 moves downward (i.e. toward a distal end 299 of the housing 250). In this arrangement, the whole attachment section 100 moves downwards while the shaft element 130 moves upwards.

The movement of the attachment section 100 superimposes with the movement of the shaft element 130 and even with a small movement of each part, a twice as large relative movement of the coupling pin 132 results relative to the attachment housing 120. Hence, the 180 degrees phase shift of the movements of the first and second connectors 210 and 220 leads in the shown example embodiment to a reduction of the required amplitude provided by the second connector element 220 to achieve a certain angular displacement of the functional element 110. In addition to this effect, the first and second connectors 210, 220 can be used, as is realized in the shown example embodiment, to superimpose two movements of the functional element 110. Here, the functional element 110 reciprocates linearly along a longitudinal axis due to the movement provided by the first connector 210 that is connected with the housing 120 of the attachment section 100 and simultaneously the functional element oscillates around the rotation axis R.

Figure 4:
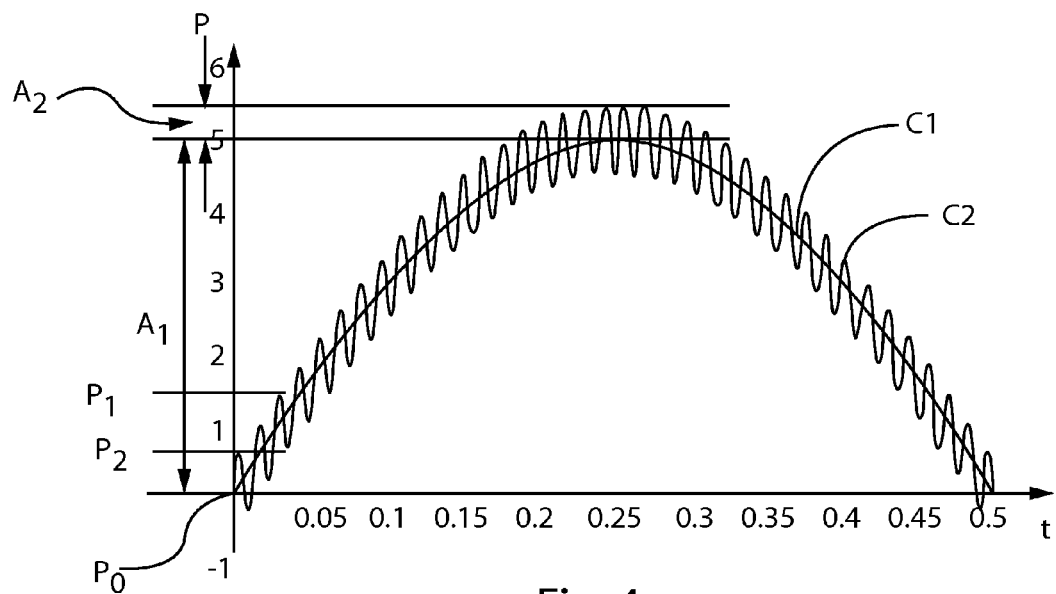
FIG. 4 is a first schematic depiction of the superimposed movements of a functional element of an attachment section of a small electric device during operation, where a relatively fast oscillatory movement of the driven functional element and a relatively slow oscillatory movement of the small electric device imposed by a user are shown.
Figure 5:
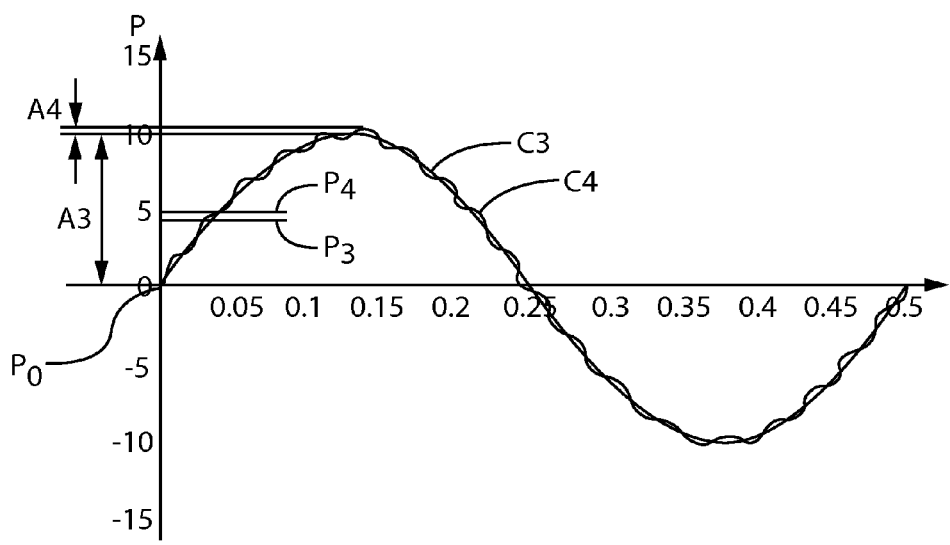
FIG. 5 is a second schematic depiction similar to FIG. 4 where in particular the amplitude of the driven movement of the functional element is lower than in FIG. 4.

During operation, a user typically grips the handle section 200 of the small electric device and may oscillate the small electric device along its longitudinal axis (as is known from a typical movement a user makes with a small electric device being an electric toothbrush—so-called scrubbing). The oscillating movement imposed by the user is likely to have a lower frequency than the frequency with which the functional element reciprocates linearly during driven operation and the oscillating movement imposed by the user is likely to have larger amplitude than the driven amplitude with which the attachment section 100 linearly reciprocates around a centre position. Such a scenario is depicted in FIGS. 4 and 5 for two different reciprocation amplitudes superimposed on the oscillatory movement imposed by a user. Without loss of generality it is assumed that the oscillatory movement imposed by the user has a sinusoidal form.

FIG. 4 shows a sinusoidal movement curve C1 (only a positive half cycle of this oscillating movement is shown) of the functional element as imposed by a user who oscillates the toothbrush along its longitudinal axis with a sinusoidal movement. The abscissa indicates the time direction t and the ordinate indicates the position P with respect to a centre position $P_0$. The user-imposed movement has peak amplitude A1 (here 5 mm at a scrubbing frequency of 1 Hz).

Curve C2 shows the movement of the functional element where the driven linear reciprocation of the attachment section along the longitudinal axis of the small electric device is superimposed with the user-imposed reciprocation. The additional driven reciprocation has peak amplitude A2 (here 0.5 mm at a frequency of 75 Hz). It can be seen that even in the upwardly and downwardly sloping parts of the user-imposed reciprocation (where the velocity of the user-imposed motion is highest), the superimposed driven reciprocation leads in total to a backwards motion of the functional element. For example, at a certain point along the generally upwardly sloping movement the position of the functional element is $P_1$ coinciding with a forward peak of the driven reciprocation movement and about a half cycle (of the driven reciprocation) later the position of the functional element is $P_2$ coinciding with a backwards peak of the driven reciprocating movement, where $P_2 < P_1$.

FIG. 5 is a similar figure as FIG. 4 (a full cycle of the super-imposed reciprocation is shown), where the user-imposed reciprocation is shown as curve C3 and the superimposed movement is shown as curve C4. Here, the user-imposed reciprocation has peak amplitude A3 (here 10 mm at a scrubbing frequency of 2 Hz) and the driven reciprocation has peak amplitude A4 (here 0.3 mm at a driven frequency of 40 Hz). It can be seen that in particular in the upwardly and downwardly sloping parts of the user-imposed reciprocation movement, the additional driven reciprocation does not lead to a noticeable backwards motion of the functional element. For example, at a certain point along the generally upwardly sloping movement, the position of the functional element is $P_3$ coinciding with a forward peak of the driven reciprocation movement and about a half cycle (of the driven reciprocation) later the position of the functional element is $P_4$ coinciding with a backwards peak of the driven reciprocating movement, where $P_3 < P_4$.

In an example embodiment, where the small electric device is an electric toothbrush and the functional element is realized as a brush head having cleaning elements that are at least partially realized as filaments (e.g. nylon, PA6.12, filaments having a diameter in the range of between about 100 μm to about 200 μm and a length in the range of about 4 mm to about 12 mm; where PA6.12 has an E-modulus of about 3600 N/mm² and typical resonance frequencies of such filaments lie in the range of between about 200 Hz to 800 Hz), a backwards motion of the functional element during the scrubbing motion done by the user may lead to an improved interdental cleaning performance as the filaments that have glided over an interdental gap will then be forced backwards in the gap again. This leads to a better interproximal penetration of the filaments into the interproximal spaces between the teeth.

Figure 6:
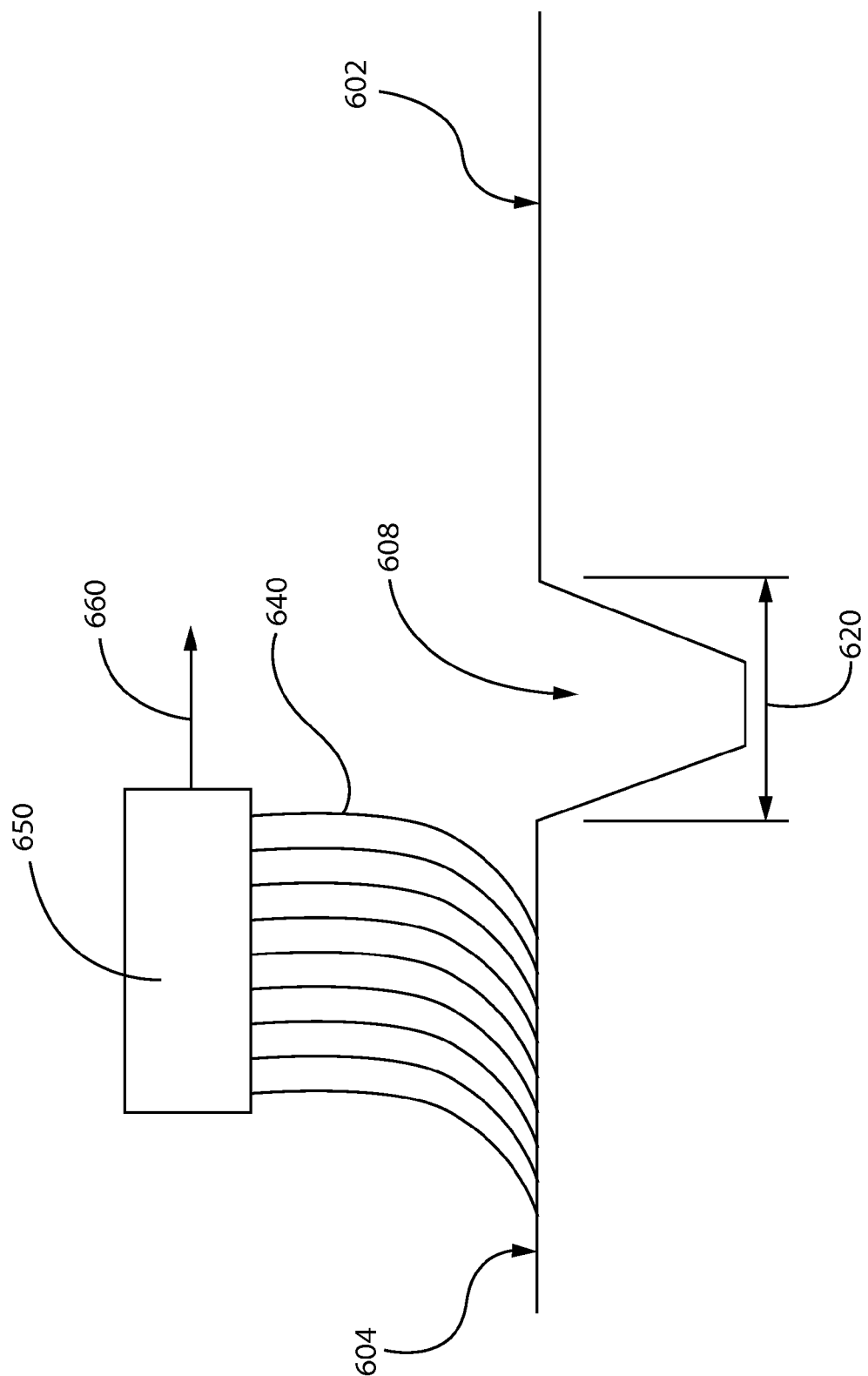
FIG. 6 is a depiction of a brush head having cleaning elements according to embodiments shown and described herein.
Figure 7:
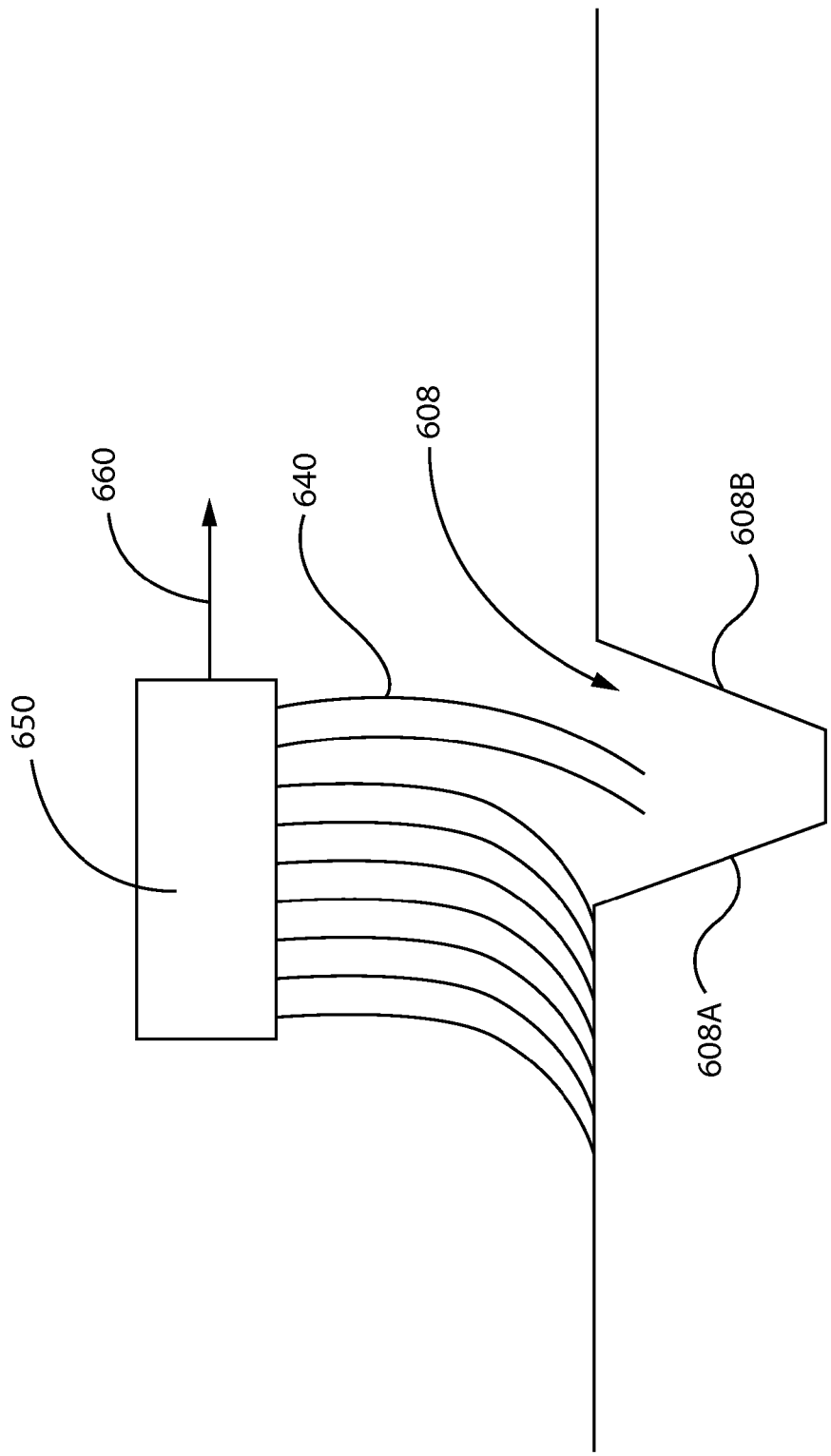
FIG. 7 is a depiction of a brush head having cleaning elements according to embodiments shown and described herein.
Figure 8:
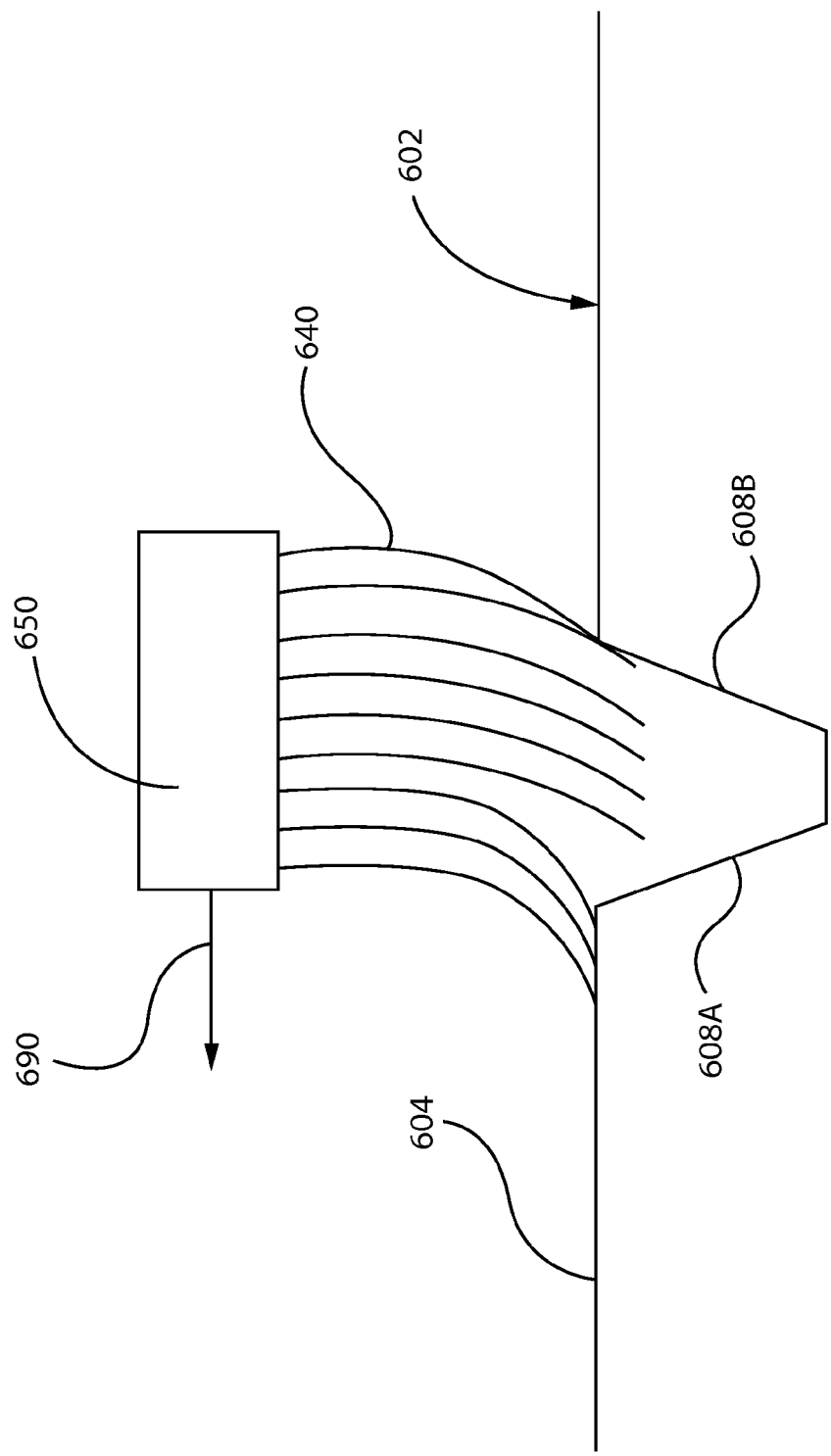
FIG. 8 is a depiction of a brush head having cleaning elements according to embodiments shown and described herein.

The backwards motion (backwards motion relative to the slow user-induced motion) brings the filaments that had entered into the interproximal spaces into contact with the teeth surfaces in the general backwards lying direction, which surfaces would at least partially have been missed in the cleaning procedure during the forwards stroke of the user-induced motion without a further driven motion. Referring to FIGS. 6-8, the movement of a brush head 650 having cleaning elements 640 is shown. In general, a user applied movement in a first direction 660 and application of pressure to the brush head 650 to a first tooth surface 604 causes the cleaning elements 640 to bend. As shown, the majority, if not all, of the cleaning element tips are in contact with the first surface 604.

In contrast, when the cleaning elements 640 enter an interdental space 608, at least a portion of the cleaning elements 640 (those in the forward most area of the brush head 650) may tend to straighten. The velocity at which the cleaning elements 640 straighten is dictated in part by the natural frequency of the cleaning elements 640. Normally, the natural frequency of the cleaning elements 640 is sufficiently larger than the user applied motion frequency such that the cleaning elements 640 can straighten to at least some extent within the interdental space 608.

As the interproximal spaces have various geometries, e.g. the interproximal space between two incisors is usually relatively small and has approximately parallel walls whereas the interproximal space between two molars is wider and the teeth are generally more curved, a single threshold value for a ratio between the peak velocity of the driven movement and the peak velocity of the user-induced motion does not lead to the same improvement of the cleaning efficiency for all interproximal geometries. A typical width of an interdental depression is lying in the range of between about 1 mm to about 3 mm.

As shown, the interdental space 608 may comprise a first wall 608A and a second wall 608B. One problem can be that as the user applied motion in the first direction 660 occurs, the cleaning elements 640 may not come into contact with the first wall 608A thereby leaving the first wall 608A uncleaned.

However, with the backward motion in a second direction 690, opposite the first direction 650, assuming the amplitude of the backward motion is substantial enough, the cleaning elements 640 can contact the first wall 608A. As described above, the backwards motion of the brush head occurs when there is a ratio of about three or more between these peak velocities (drive frequency to user frequency) leads to a noticeable backwards motion of the bristles during the backwards driven motion also in the steep slope of the user-induced motion.

The frequency of the typical user-imposed scrubbing motion is assumed to lie in the range of between about 1 Hz to about 2 Hz even though some users may scrub with a higher or lower frequency. The typical peak amplitude of the user-imposed scrubbing motion is assumed to lie in the range of between about 5 mm to about 10 mm. Based on these parameters, the average (absolute, i.e. neglecting the sign) velocity $v_{avg}$ of the functional element that is moved with such a frequency and peak amplitude is given by 4 multiplied with the peak amplitude value multiplied with the frequency value, $v_{avg} = 4 \cdot f \cdot A$, where f is the frequency value and A is the peak amplitude value. The resulting typical average absolute velocity of the user-imposed movement lies in a range of between about 20 mm/s to about 80 mm/s The peak velocity $v_p$, $v_p = 2\pi \cdot f \cdot A$, where f is the frequency value and A is the peak amplitude value. In the steep slopes of the sinusoidal movement, the peak velocity, $v_p$, lies in a range of between about 31 mm/s to 126 mm/s. An average absolute velocity $v_{avg}$ may be in the range of between about 40 mm/s to about 50 mm/s (the peak velocity $v_p$ then lying in the range of between about 63 mm/s to about 79 mm/s) may be considered as a sub-range in which a relatively high percentage of scrubbing motions imposed by users lie. The average absolute velocity $v_{avg}$ and the peak velocity $v_p$ relate to each other as $v_p = 2\pi/4 \cdot v_{avg} = 1.57075 \cdot v_{avg}$.

In an example embodiment, the first connector provides a peak amplitude that lies in the range of about 0.1 mm to about 1.0 mm, optionally a peak amplitude lying in the range of between about 0.3 mm and about 0.5 mm. The reciprocation frequency may be chosen to lie in the range of between about 50 Hz to about 250 Hz, optionally in the range of between about 100 Hz to about 200 Hz and further optionally in a range of about 140 Hz and about 180 Hz and yet further optionally in the range of between about 150 Hz to about 170 Hz. The average absolute velocity $v_{avg}$ of the functional element then ranges from about 20 mm/s to about 1000 mm/s or for the narrowest optional values of between about 180 mm/s to about 340 mm/s. For some users average absolute velocities above a certain threshold lead to discomfort and/or gum irritation. Such a threshold can depend on the kind of filament, its characteristics (e.g. end rounding quality) and on the specific user. Typically, average absolute velocities above 500 mm/s tend to be felt as discomforting by at least a noticeable percentage of users.

As has been stated, improved interdental cleaning is likely to occur when the driven reciprocation has an average absolute velocity $v_z$ that is at least about three times the average absolute velocity $v_h$ of the user-imposed reciprocation, hence for $v_h$=20 mm/s this would require $v_z$≥60 mm/s or for $v_h$=80 mm/s this would require $v_z$≥240 mm/s. When $v_h$ lies in the range of between about 40 mm/s to about 60 mm/s, the required minimum average absolute velocity $v_h$ ranges from about 120 mm/s to about 180 mm/s.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An electric toothbrush having a handle section and an attachment section, the handle section comprising:
   a handle housing in which a drive unit is disposed;
   a first connector element extending from the handle housing being adapted for connection with an attachment section, the first connector element being coupled to a first drive of the drive unit; and
   a second connector element extending from the handle housing being adapted for connection with the attachment section, the second connector element being coupled to a second drive of the drive unit;
   wherein the first connector element linearly reciprocates relative to the handle housing during operation and the second connector element linearly reciprocates relative to the handle housing with a 180 degrees phase shift with respect to the first connector element;
   wherein the attachment section is coupled via a coupling to the first connector element and the second connector element, wherein the coupling is a detachable coupling;
   wherein the attachment section includes an attachment housing and a functional element, wherein the attachment housing is coupled to the first connector element such that the attachment housing linearly reciprocates together with the first connector element during operation, and the functional element is movably mounted at the attachment housing;
   wherein the functional element is mounted for oscillatory rotation around a rotation axis that is essentially perpendicular to a longitudinal axis along which the first connector element linearly reciprocates;
   whereby during operation the functional element simultaneously reciprocates in a direction of the longitudinal axis and oscillates around the rotation axis that is essentially perpendicular to a longitudinal axis;
   wherein the drive unit is a resonant drive and the first drive is a first moving part of the resonant drive and the second drive is a second moving part of the resonant drive;
   wherein the first and second moving parts are coupled to the handle housing and to each other by a spring arrangement; and
   wherein the average absolute velocity of the first connector element during operation lies in the range of between about 100 mm/s to about 240 mm/s.

2. The electric toothbrush in accordance with claim 1, wherein the first connector element and the second connector element are essentially coaxially arranged.

3. The electric toothbrush in accordance with claim 1, wherein the first connector element moves during operation with a frequency in the range of between about 150 Hz to about 170 Hz.

4. The electric toothbrush in accordance with claim 1, wherein the attachment section comprises a gear unit for transforming the linear reciprocating motion provided by the second connector element.

5. The electric toothbrush in accordance with claim 4, wherein the gear unit comprises a shaft element that is eccentrically coupled to the functional element with respect to the rotation axis on a first end of the shaft element and that is coupled to the second connector element at a second end of the shaft element.

6. The electric toothbrush in accordance with claim 4, wherein the first connector element provides a peak amplitude in a range of between about ±0.2 mm and about ±0.5 mm during operation with respect to a centre position.

7. The electric toothbrush in accordance with claim 6, wherein the ratio between the peak amplitudes provided by the first connector element and the second connector element during operation is in a range of between about 0.6 and about 1.0.

8. The electric toothbrush in accordance of claim 6, wherein the average absolute velocity of the first connector element during operation lies in the range of between about 120 mm/s to about 240 mm/s.

* * * * *